United States Patent
Ravi et al.

(10) Patent No.: US 9,604,995 B2
(45) Date of Patent: Mar. 28, 2017

(54) PROCESS FOR THE PREPARATION OF OLANZAPINE PAMOATE

(71) Applicant: NEULAND LABORATORIES LIMITED, Hyderabad (IN)

(72) Inventors: Ponnaiah Ravi, Madurai (IN); Praveenkumar Neela, Hyderabad (IN); Kashyap Ravindrabhai Wadekar, Ahmedabad (IN); Kubireddy Vigneshwar Reddy, Hyderabad (IN); Sampath Kumar Laxmalla, Hyderabad (IN)

(73) Assignee: NEULAND LABORATORIES LIMITED, Hyderabad (IN)

( * ) Notice: Subject to any disclaimer, the term of this patent is extended or adjusted under 35 U.S.C. 154(b) by 12 days.

(21) Appl. No.: 14/767,296

(22) PCT Filed: Apr. 8, 2013

(86) PCT No.: PCT/IN2013/000232
§ 371 (c)(1),
(2) Date: Aug. 12, 2015

(87) PCT Pub. No.: WO2014/125500
PCT Pub. Date: Aug. 21, 2014

(65) Prior Publication Data
US 2016/0002258 A1    Jan. 7, 2016

(30) Foreign Application Priority Data

Feb. 13, 2013   (IN) .............................. 620/CHE/2013

(51) Int. Cl.
*C07D 495/14*   (2006.01)
*C07D 495/04*   (2006.01)
*C07C 51/41*    (2006.01)

(52) U.S. Cl.
CPC ............ *C07D 495/04* (2013.01); *C07C 51/41* (2013.01)

(58) Field of Classification Search
CPC ..................................................... C07D 495/14
USPC ........................................................... 549/43
See application file for complete search history.

(56) References Cited

FOREIGN PATENT DOCUMENTS

WO      WO0018408 A1      4/2000
WO      WO2011091142 A2   7/2011

*Primary Examiner* — Douglas M Willis
(74) *Attorney, Agent, or Firm* — Ling Wu; Stephen Yang; Ling and Yang Intellectual Property

(57) ABSTRACT

An improved process for preparation of Olanzapine pamoate monohydrate from Olanzpaine is disclosed which comprises mixing at room temperature a solution of olanzapine prepared in water in presence of an acid, with a solution of pamoic acid prepared in water in presence of a base; stirring and maintaining the reaction mixture for a sufficient time till precipitation of solid and drying the solid to obtain olazapine pamoate monohydrate.

8 Claims, 1 Drawing Sheet

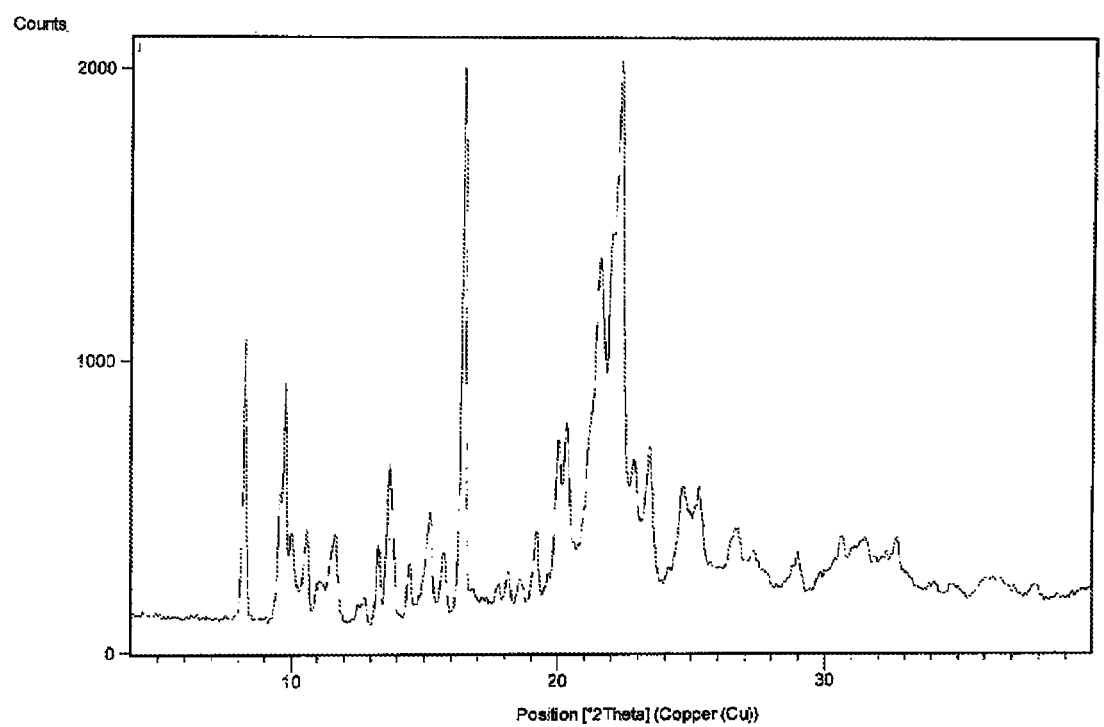

PROCESS FOR THE PREPARATION OF OLANZAPINE PAMOATE

FIELD OF THE INVENTION

The invention relates to an improved process for preparation of olanzapine pamoate. More particularly, invention relates to an improved process for preparation of olanzapine pamoate monohydrate from olanzapine.

BACKGROUND OF THE INVENTION

Olanzapine pamoate depot is the third atypical antipsychotic drug to be available as a long-acting intramuscular injection. It was first disclosed in PCT publication WO00/18408 and is structurally represented as below:

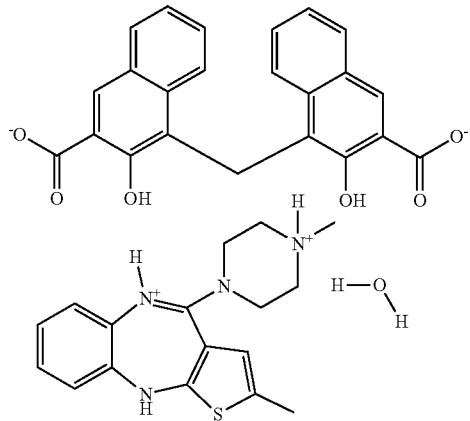

It is developed by Eli Lilly and is approved in USA and Europe for the treatment of schizophrenia. Olanzapine long acting injection (LAI) is a salt of pamoic acid and olanzapine that is suspended in an aqueous solution and is injected into the gluteal muscle. Once injected in the gluteal muscle, the two components of the salt slowly dissociate into separate molecular compounds i.e. olanzapine and pamoic acid.

Rate of dissolution of the salt is slow, allowing for a gradual release of olanzapine into the blood circulation over 2 to 4 weeks.

PCT publication WO2011/091142 assigned to Teva Pharma discloses a process for preparation of olanzapine pamoate monohydrate from olanzpaine, wherein the process comprises refluxing olanzapine with pamoic acid in water for 6 hours, cooling the reaction mixture to 50° C. and stirring at the same temperature for 72 hours.

Further, PCT publication WO0018408 disclose a process for preparation of olanzapine pamoate monohydrate from olanzpaine which comprises mixing olanzapine with pamoic acid in the solvents such as N-Dimethyl sulfoxide, tetrahydrofuran, DMSO, acetone and the reaction time is less than one hour.

The processes for preparation of olanzapine pamoate monohydrate from olanzapine as described in the above prior arts require costly solvents and requires longer reaction time. Therefore, there exists a need to have a simple, cost-effective, efficient and commercially viable process for industrial scale preparation of olanzapine pamoate by employing cost effective solvents and requiring minimum reaction time for commercial production.

OBJECT OF THE INVENTION

The primary object of the invention is to provide an improved process for preparation of olanzapine pamoate from olanzapine.

Another object of the invention is to provide an improved cost effective and commercially viable process for industrial scale preparation of olanzapine pamoate monohydrate.

SUMMARY OF THE INVENTION

Accordingly, the invention provides an improved process for preparation of olanzapine pamoate monohydrate from olanzapine.

The process comprises:
(i) preparing a solution of olanzapine in water in the presence of an acid;
(ii) preparing a solution of pamoic acid in water in presence of a base;
(iii) mixing the solution pamoic acid prepared in step (ii) with the olanzapine solution prepared in step (i);
(iv) maintaining the reaction mixture at the same temperature for a sufficient time till precipitation of a solid;
(v) optionally, filtering the reaction mass;
(vi) drying the solid to get olanzapine pamoate monohydrate.

The olanzapine employed in step (i) may be olanzapine form-I or any polymorphic form of olanzapine or any solvate of the olanzapine.

The acid in step (i) may be an organic acid or an inorganic acid.

The base in step (ii) may be an organic base or an inorganic base.

The steps (i) to (iv) are performed between room temperature to 100° C.

Inventors of the present invention surprisingly found a commercially efficient process for the preparation of olanzapine pamoate from olanzapine, employing water as a solvent with shorter reaction time.

The desired particle size of the olanzapine pamoate monohydrate obtained from the process of the invention may be obtained by any of the conventionally known mechanical processes such as cutting, chipping, crushing, grinding, milling and micronizing.

BRIEF DESCRIPTION OF THE DRAWINGS

FIG. 1 represents typical X-ray powder diffraction pattern of the olanzapine pamoate monohydrate of the invention.

DETAILED DESCRIPTION OF THE INVENTION

Detailed embodiments of the present invention are disclosed herein below. However, it is to be understood that the disclosed embodiments are merely exemplary of the invention, which can be embodied in various forms. The scope of the invention is not limited to the disclosed embodiments and terms and phrases used herein are not intended to be limiting but rather to provide an understandable description of the invention. The invention is defined by claims appended hereto.

The invention provides a process for preparation of olanzapine pamoate monohydrate from Olanzpaine.

In an exemplary embodiment, the process comprises the steps of:

(i) preparing a solution of olanzapine in water in presence of an acid;

(ii) preparing a solution of pamoic acid in water in the presence of a base;

(iii) mixing the pamoic acid solution prepared in step (ii) with the olanzapine solution prepared in step (i);

(iv) maintaining the reaction mixture at the same temperature for a sufficient time till precipitation of the solid;

(v) optionally, filtering the reaction mass;

(vi) drying the solid to get olanzapine pamoate monohydrate.

The olanzapine employed in step (i) may be olanzapine form-I or any polymorphic form of olanzapine or any solvate of the olanzapine.

In an exemplary embodiment, the step (i) of the process comprises dissolving acid addition salt of olanzapine selected from olanzapine Form-I, any polymorphic form of olanzapine or any solvate of olanzapine in water or a solvent to obtain a clear solution.

The step (i) may be carried out at temperatures between room temperature to 100° C., preferably at temperature between 20-35° C.

In the same embodiment of the invention, the step (ii) of the process comprises dissolving any alkaline salt of pamoic acid in water or a solvent to obtain a clear solution.

The step (ii) of the process may be carried out at temperatures between room temperature to 100° C., preferably at temperature between 20-35° C.

In the same embodiment, the step (iii) of the process comprises mixing the pamoic acid solution prepared in step (ii) and the olanzapine solution prepared in step (i).

In one embodiment of the invention, the mixing of pamoic acid solution with olanzapine solution may be done by adding the pamoic acid solution prepared in step (ii) into the Olanzapine solution prepared in step (i).

In another embodiment, the mixing of pamoic acid solution with olanzapine solution may be done by adding the olanzapine solution prepared in step (i) into the pamoic acid solution prepared in step (ii).

The step (iii) may be carried out at temperatures between room temperature to 100° C., preferably at temperature between 20-35° C.

In step (iv) the reaction mixture is maintained at temperatures between room temperature to 100° C., preferably at temperature between 20-35° C.

According to the present invention, the step (i) and step (ii) of the process for the preparation of olanzapine pamoate monohydrate from olanzpaine may be carried out optionally in the presence of a solvent or mixtures thereof, wherein the solvent employed is selected from the group comprising hydrocarbons such as pentane, hexane, heptanes, octane, petroleum ether; aromatic hydrocarbons such as toluene, xylenes; chlorinated hydrocarbons such as chlorobenzene, o-dichlorobenzene, 1,2-dichloroethane; esters such as ethyl acetate; ethers such as tetrahydrofuran, diethyl ether, methyl tert-butyl ether, 1,4-dioxane, dimethoxyethane; N,N-dimethyl formamide, dimethyl sulfoxide, N,N-dimethyl acetamide; alcohols such as methanol, ethanol, propanol, isopropanol, butanol, t-butanol; or mixtures thereof.

In an exemplary embodiment, the acid in step (i) may be an organic acid or an inorganic acid. The organic acid in step (i) of the process may be selected from the group comprising of mono- and polycarboxylic acids having a linear or cyclic aliphatic group with 2 to 50 carbon atoms such as acetic acid, propionic acid, butyric acid, valeric acid, hexanoic acid, heptanoic acid, octanoic acid, nonanoic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, cyclopentanecarboxylic acid, cyclohexanecarboxylic acid, cyclopentenecarboxylic acid, cyclohexenecarboxylic acid, condensed aliphatic heterocyclic group with 2 to 14 carbon atoms and at least one heteroatom (preferably 1 to 3 heteroatoms) such as a nitrogen atom, an oxygen atom and/or a sulfur atom such as 2-azetidinecarboxylic acid, 2-pyrrolidinecarboxylic acid (proline), 3-pyrrolidinecarboxylic acid, 2-piperidinecarboxylic acid, 3-piperidinecarboxylic acid, 4-piperidinecarboxylic acid and piperazine-2-carboxylic acid.

The inorganic acid in step (i) of the process of the invention may be selected from the group comprising of sulfuric acid, phosphoric acid, nitric acid, hydrochloric acid and hydrobromic acid.

The base employed in carrying out the step (ii) of the process of the invention is selected from inorganic and organic bases.

In a general embodiment of the invention, the organic bases in step (ii) of the process may be selected from the group comprising of isopropyl amine, diisopropyl amine, diisopropyl ethyl-amine, N-methyl morpholine, N-methyl piperidine, N-methyl piperazine, N-methyl pyridine, DBU, DABCO and triethylamine.

The inorganic bases in step (ii) of the process of the invention may be selected from the group comprising of alkali metals such as sodium, potassium, lithium; alkali metal carbonates such as sodium carbonate, potassium carbonate, cesium carbonate, lithium carbonate; alkali metal bicarbonates such as sodium bicarbonate, potassium bicarbonate, lithium bicarbonate, cesium bicarbonate; alkali metal hydroxides such as sodium hydroxide, calcium hydroxide, potassium hydroxide; metal alkoxides such as alkoxides of sodium, lithium or potassium, sodium tert-butoxide; alkali metal hydrides such as sodium hydride; alkali metal chlorides such as calcium chloride; alkali metal acetates acetate of calcium, potassium or Lithium; and ammonia source such as ammonium carbonate, ammonia, ammonium hydroxide.

Inventors of the present invention surprisingly found a commercially efficient process for the preparation of olanzapine pamoate from olanzapine employing water as a solvent with shorter reaction time.

The desired particle size of the olanzapine pamoate monohydrate obtained from the process of the invention may be obtained by any of the conventionally known mechanical processes such as cutting, chipping, crushing, grinding, milling and micronizing. In one embodiment, the desired particle size distribution of the the olanzapine pamoate monohydrate is obtained by milling of the olanzapine pamoate monohydrate obtained from the process of the invention described in above paragraphs.

Smaller particle size correlates with clarity of the aqueous liquid dilution compositions containing the diluted concentrates. For example, a liquid with a smaller particle size is more clear than a liquid with a larger particle size.

The following examples are provided to enable one skilled in the art to practice the invention and merely illustrate the process of the invention. However, it is not intended in any way to limit the scope of the present invention.

EXAMPLES

Example 1: Preparation of Olanzapine Pamoate Monohydrate by NaOH and HCl

Pamoic acid (6.2 g, 16 mmol) was mixed with water (100 ml) and NaOH (1.28 g, 32 mmol) to get a clear solution.

Olanzapine (5.0 g, 16 mmol) was mixed with water (100 ml) and aqueous hydrochloric acid (3.65 g, 32 mmol) to get a clear solution. The prepared disodium pamoate solution was added into the prepared olanzapine solution at room temperature of 25-30° C. and the reaction mixture was stirred for 30 minutes at the same temperature. The resultant yellow solid was filtered, washed with water (15 ml) and dried in a vacuum oven at 40-45° C. % Yield: 93%

Example 2: Preparation of Olanzapine Pamoate Monohydrate by NaOH and Acetic Acid Pamoic acid (6.2 g, 16 mmol) was mixed with water (100 ml) and NaOH (1.28 g, 32 mmol) to get a clear solution. Olanzapine (5.0 g, 16 mmol) was mixed with water (100 ml) and aqueous acetic acid (32 mmol) to get a clear solution. The prepared disodium pamate solution was added in to the prepared olanzapine solution at room temperature of 25-30° C. and the reaction mixture was stirred for 30 minutes at the same temperature. The resultant yellow solid was filtered, washed with water (15 ml) and dried in a vacuum oven at 40-45° C. Yield: 96%

Example 3: Preparation of Olanzapine Pamoate Monohydrate by NaOH and Sulfuric Acid Pamoic acid (6.2 g, 16 mmol) was mixed with water (100 ml) and NaOH (1.28 g, 32 mmol) to get a clear solution. Olanzapine (5.0 g, 16 mmol) was mixed with water (100 ml) and aqueous sulfuric acid (16 mmol) to get a clear solution. The prepared disodium pamate solution was added in to the prepared olanzapine solution at room temperature of 25-30° C. and the reaction mixture was stirred for 30 minutes. The resultant yellow solid was filtered, washed with water (15 ml) and dried in a vacuum oven at 40-45° C. Yield: 89%

Example-4: Preparation of Olanzapine Pamoate Monohydrate by Ammonia and HCl

Pamoic acid (6.2 g, 16 mmol) was mixed with water (100 ml) and aqueous ammonia (7.5 g, 32 mmol) to get a clear solution. Olanzapine (5.0 g, 16 mmol) was mixed with water (100 ml) and aqueous hydrochloric acid (3.65 g, 32 mmol) to get a clear solution. The prepared disodium pamoate solution was added into the prepared olanzapine solution at room temperature of 25-30° C. and the reaction mixture was stirred for 30 minutes at the same temperature. The resultant yellow solid was filtered, washed with water (15 ml) and dried in a vacuum oven at 40-45° C. % Yield: 97%

Example-5: Preparation of Olanzapine Pamoate Monohydrate by NH$_4$OH and Acetic Acid Pamoic acid (6.2 g, 16 mmol) was mixed with water (100 ml) and aqueous ammonia (7.5 g, 32 mmol) to get a clear solution. Olanzapine (5.0 g, 16 mmol) was mixed with water (100 ml) and acetic acid (1.92 g, 32 mmol) to get a clear solution. The prepared disodium pamoate solution was added into the prepared olanzapine solution at room temperature of 25-30° C. and the reaction mixture was stirred for 4 hours minutes at the same temperature. The resultant yellow solid was filtered, washed with water (15 ml) and dried in a vacuum oven at 50-55° C. % Yield: 90%

Example-6: Preparation of Olanzapine Pamoate Monohydrate by NH$_4$OH and Sulphuric Acid Pamoic acid (6.2 g, 16 mmol) was mixed with water (100 ml) and ammonium hydroxide (7.5 g, 32 mmol) to get a clear solution. Olanzapine (5.0 g, 16 mmol) was mixed with water (100 ml) and sulfuric acid (1.57 g, 16 mmol) to get a clear solution. The prepared disodium pamoate solution was added into the prepared olanzapine solution at room temperature of 25-30° C. and the reaction mixture was stirred for 4 hours minutes at the same temperature. The resultant yellow solid was filtered, washed with water (15 ml) and dried in a vacuum oven at 40-45° C. % Yield: 92%

Example 7: Preparation of Olanzapine Pamoate Monohydrate by KOH and HCl

Pamoic acid (6.2 g, 16 mmol) was mixed with water (100 ml) and KOH (2.10 g, 32 mmol) to get a clear solution. Olanzapine (5.0 g, 16 mmol) was mixed with water (100 ml) and hydrochloric acid (3.65 g, 32 mmol) to get a clear solution. The prepared disodium pamoate solution was added into the prepared olanzapine solution at room temperature of 25-30° C. and the reaction mixture was stirred for 4 hours minutes at the same temperature. The resultant yellow solid was filtered, washed with water (30 ml) and dried in a vacuum oven at 40-45° C. % Yield: 93%

Example 8: Preparation of Olanzapine Pamoate Monohydrate by K$_2$CO$_3$ and HCl Pamoic acid (6.2 g, 16 mmol) was mixed with water (100 ml) and potassium carbonate (2.20 g, 16 mmol) to get a clear solution. Olanzapine (5.0 g, 16 mmol) was mixed with water (100 ml) and hydrochloric acid (3.65 g, 32 mmol) to get a clear solution. The prepared disodium pamoate solution was added into the prepared olanzapine solution at room temperature of 25-30° C. and the reaction mixture was stirred for 4 hours minutes at the same temperature. The resultant yellow solid was filtered, washed with water (15 ml) and dried in a vacuum oven at 40-45° C. % Yield: 93%

Example 9: Preparation of Olanzapine Pamoate Monohydrate by Triethyl Amine and HCl Pamoic acid (6.2 g, 16 mmol) was mixed with water (100 ml) and triethylamine (3.36 g) to get a clear solution. Olanzapine (5.0 g, 16 mmol) was mixed with water (100 ml) and hydrochloric acid (3.8 g) to get a clear solution. The prepared disodium pamoate solution was added into the prepared olanzapine solution at room temperature of 25-30° C. and the reaction mixture was stirred for 4 hours minutes at the same temperature. The resultant yellow solid was filtered, washed with water (40 ml) and dried in a vacuum oven at 40-45° C. % Yield: 90%

Example 10: Preparation of Olanzapine Pamoate Monohydrate by Pyridine and HCl Pamoic acid (6.2 g, 16 mmol) was mixed with water (100 ml) and pyridine (27.96 g) to get a clear solution. Olanzapine (5.0 g, 16 mmol) was mixed with water (100 ml) and hydrochloric acid (3.65 g) to get a clear solution. The prepared disodium pamoate solution was added into the prepared olanzapine solution at room temperature of 25-30° C. The pH of the reaction mixture was adjusted to 5.1 and then the reaction mixture was stirred for 4 hours at 25-30° C. The resultant yellow solid was filtered, washed with water (30 ml) and dried in a vacuum oven at 40-45° C. % Yield: 89%

Example 11: Preparation of Olanzapine Pamoate Monohydrate by Lithum Hydroxide Mono Hydrate and HCl Pamoic acid (6.2 g, 16 mmol) was mixed with water (100 ml) and lithium hydroxide (1.32 g 32 mmol) to get a clear solution. Olanzapine (5.0 g, 16 mmol) was mixed with water (100 ml) and hydrochloric acid (3.65 g, 32 mmol) to get a clear solution. The prepared disodium pamoate solution was added into the prepared olanzapine solution at room temperature of 25-30° C. and the reaction mixture was stirred for 4 hours minutes at the same temperature. The resultant yellow solid was filtered, washed with water (30 ml) and dried in a vacuum oven at 40-45° C. % Yield: 90%.

We claim:

1. A process for the preparation of olanzapine pamoate monohydrate, comprising the following steps:
   (i) preparing an aqueous solution of olanzapine, or a polymorph or solvate thereof, in the presence of an acid;
   (ii) preparing an aqueous solution of pamoic acid in the presence of a base;
   (iii) mixing the aqueous solution of pamoic acid prepared in step (ii) with the aqueous solution of olanzapine prepared in step (i);
   (iv) stirring the aqueous mixture formed in step (iii) to induce precipitation;
   (v) optionally, isolating the precipitate formed in step (iv) by filtration; and
   (vi) drying the precipitate formed in step (iv) to obtain olanzapine pamoate monohydrate.

2. The process as claimed in claim 1, wherein the olanzapine of step (i) is a polymorph or a solvate thereof.

3. The process as claimed in claim 1, wherein the acid of step (i) is an organic acid or inorganic acid.

4. The process as claimed in claim 3, wherein the organic acid is selected from the group consisting of mono- and polycarboxylic acids having a linear or cyclic aliphatic group with 2 to 50 carbon atoms or a condensed aliphatic heterocyclic group with 2 to 14 carbon atoms and one or more nitrogen, oxygen and/or sulfur heteroatoms.

5. The process as claimed in claim 3, wherein the inorganic acid of step (i) is selected from the group consisting of sulfuric acid, phosphoric acid, nitric acid, hydrochloric acid and hydrobromic acid.

6. The process as claimed in claim 1, wherein the base of step (ii) is selected from an inorganic or organic base.

7. The process as claimed in claim 6, wherein the organic base is selected from the group consisting of isopropyl amine, diisopropyl amine, diisopropyl ethyl amine, N-methylmorpholine, N-methylpiperidine, N-methylpiperazine, N-methylpyridine, 1,8-diazabicyclo[5.4.0]undec-7-ene, 1,4-diazabicyclo[2.2.2]octane and triethylamine.

8. The process as claimed in claim 6, wherein the inorganic base is selected from the group consisting of alkali metal carbonates, alkali metal bicarbonates, alkali metal hydroxides, alkali metal alkoxides, alkali metal chlorides, alkali metal hydrides, alkali metal acetates and ammonia.

* * * * *